(12) United States Patent
Nishimura et al.

(10) Patent No.: US 10,932,681 B2
(45) Date of Patent: Mar. 2, 2021

(54) OPTICAL UNIT, MEASUREMENT SYSTEM, AND MEASUREMENT METHOD

(71) Applicant: SONY CORPORATION, Tokyo (JP)

(72) Inventors: Takuya Nishimura, Tokyo (JP); Kota Aizawa, Tokyo (JP); Yoshihiro Wakita, Tokyo (JP)

(73) Assignee: SONY CORPORATION, Tokyo (JP)

(*) Notice: Subject to any disclaimer, the term of this patent is extended or adjusted under 35 U.S.C. 154(b) by 0 days.

(21) Appl. No.: 15/544,069

(22) PCT Filed: Dec. 3, 2015

(86) PCT No.: PCT/JP2015/083970
§ 371 (c)(1),
(2) Date: Jul. 17, 2017

(87) PCT Pub. No.: WO2016/132628
PCT Pub. Date: Aug. 25, 2016

(65) Prior Publication Data
US 2017/0347900 A1    Dec. 7, 2017

(30) Foreign Application Priority Data
Feb. 17, 2015   (JP) .............................. JP2015-028252

(51) Int. Cl.
*A61B 5/0295*   (2006.01)
*A61B 5/026*    (2006.01)
*A61B 5/00*     (2006.01)

(52) U.S. Cl.
CPC ............ *A61B 5/0295* (2013.01); *A61B 5/004* (2013.01); *A61B 5/0037* (2013.01);
(Continued)

(58) Field of Classification Search
None
See application file for complete search history.

(56) References Cited

U.S. PATENT DOCUMENTS

| 4,891,738 A | * | 1/1990 | Richardson | ........... F21S 10/007 362/282 |
| 5,113,332 A | * | 5/1992 | Richardson | ............... F21V 9/40 362/282 |

(Continued)

FOREIGN PATENT DOCUMENTS

| JP | 10-243936 A | 9/1998 |
| JP | 10-290791 A | 9/1998 |

(Continued)

OTHER PUBLICATIONS

International Search Report and Written Opinion of PCT Application No. PCT/JP2015/083970, dated Mar. 1, 2016, 02 pages of English Translation and 08 pages of ISRWO.

*Primary Examiner* — Kara E. Geisel
*Assistant Examiner* — Jarreas C Underwood
(74) *Attorney, Agent, or Firm* — Chip Law Group

(57) ABSTRACT

Provided is an optical unit that radiates a coherent light such that the coherent light is incident in a target region of speckle image capturing in accordance with a pattern that includes a bright region and a dark region located uniformly in at least one direction in the target region. Provided is a measurement system including: an optical unit that radiates a coherent light such that the coherent light is incident in a target region in accordance with a pattern that includes a bright region and a dark region located uniformly in at least one direction in the target region; a light reception unit that receives a reflected light of the coherent light in the target region; and an imaging unit that captures an image of a speckle included in the reflected light.

11 Claims, 11 Drawing Sheets

(52) U.S. Cl.
CPC .......... *A61B 5/0066* (2013.01); *A61B 5/0077* (2013.01); *A61B 5/026* (2013.01); *A61B 5/0261* (2013.01)

(56) References Cited

U.S. PATENT DOCUMENTS

| | | | | |
|---|---|---|---|---|
| 5,339,817 | A * | 8/1994 | Nilsson | A61B 5/0261 600/473 |
| 5,516,605 | A * | 5/1996 | Hwang | G03F 7/30 430/5 |
| 5,572,368 | A * | 11/1996 | Yokota | G02B 3/005 359/710 |
| 5,733,315 | A * | 3/1998 | Burdette | A61B 18/18 601/3 |
| 5,771,412 | A * | 6/1998 | Kobayashi | G02B 7/32 396/106 |
| 5,798,840 | A * | 8/1998 | Beiting | G01N 21/4795 356/435 |
| 5,934,794 | A * | 8/1999 | Hutton | F21S 10/007 362/283 |
| 5,988,835 | A * | 11/1999 | Allen | F21S 10/007 362/284 |
| 6,122,042 | A * | 9/2000 | Wunderman | A61B 1/05 356/343 |
| 6,353,226 | B1 * | 3/2002 | Khalil | A61B 5/14532 250/339.11 |
| 6,486,939 | B2 * | 11/2002 | Lin | G03F 1/26 250/548 |
| 6,490,028 | B1 * | 12/2002 | Ditto | G01B 11/026 356/4.09 |
| 6,508,774 | B1 * | 1/2003 | Acker | A61B 8/0833 600/439 |
| 7,498,811 | B2 * | 3/2009 | MacFarlane | G01R 33/28 324/318 |
| 8,494,228 | B2 * | 7/2013 | Fujii | A61B 5/489 382/115 |
| 8,531,650 | B2 * | 9/2013 | Feldkhun | G01B 11/2527 356/4.01 |
| 8,976,441 | B2 * | 3/2015 | Hewlett | G02B 26/0833 359/290 |
| 9,606,237 | B2 * | 3/2017 | Herschbach | G01S 17/48 |
| 10,194,803 | B2 * | 2/2019 | Masumura | G01N 21/4795 |
| 2012/0236288 | A1 * | 9/2012 | Stanley | G01B 11/2513 356/4.01 |
| 2014/0176730 | A1 * | 6/2014 | Kaji | H04N 9/3182 348/189 |
| 2015/0323311 | A1 * | 11/2015 | Muijs | A61B 5/0059 356/28.5 |

FOREIGN PATENT DOCUMENTS

| | | |
|---|---|---|
| JP | 10-243936 A | 11/1998 |
| JP | 10-290791 A | 11/1998 |
| WO | 2009/122931 A1 | 10/2009 |
| WO | 2013/185937 A1 | 12/2013 |
| WO | WO 2013/185937 * | 12/2013 |

* cited by examiner

FIG. 9(a)
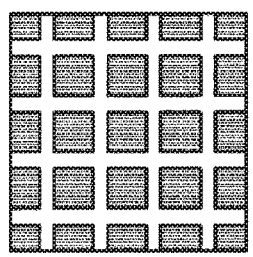
FIG. 9(b)
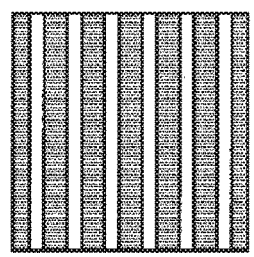
FIG. 9(c)
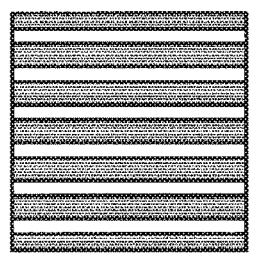
FIG. 9(d)
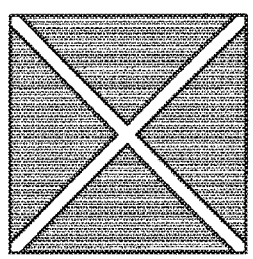
FIG. 9(e)
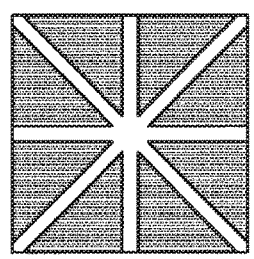
FIG. 9(f)
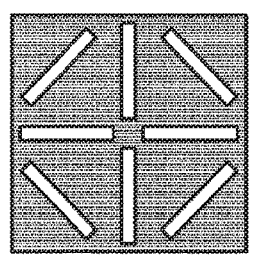
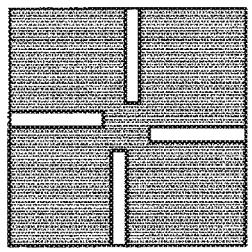
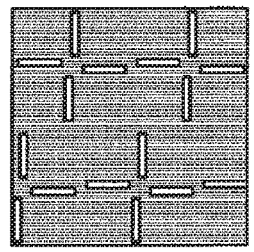
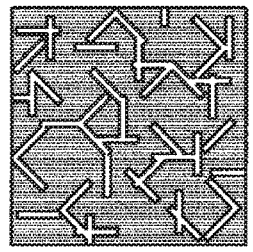
FIG. 9(g)
FIG. 9(h)
FIG. 9(i)

OPTICAL UNIT, MEASUREMENT SYSTEM, AND MEASUREMENT METHOD

CROSS REFERENCE TO RELATED APPLICATIONS

This application is a U.S. National Phase of International Patent Application No. PCT/JP2015/083970 filed on Dec. 3, 2015, which claims priority benefit of Japanese Patent Application No. JP 2015-028252 filed in the Japan Patent Office on Feb. 17, 2015. Each of the above-referenced applications is hereby incorporated herein by reference in its entirety.

TECHNICAL FIELD

The present disclosure relates to an optical unit, a measurement system, and a measurement method.

BACKGROUND ART

When coherent light such as laser is radiated toward epidermis of a living body or the like, reflected and diffused lights interfere with each other to form a granular image which is called speckle. There is a known technology for measuring a state of the epidermis of the living body for example, more specifically blood flow beneath the epidermis, by capturing an image of this speckle (speckle image capturing). Patent Literature 1 describes a technology in which electrical signals from two sets of photoelectric sensors are sampled as speckle time-series data of a measurement region, and a two-dimensional blood flow rate and a blood flow direction are measured on the basis of cross-correlation of the time-series data and a phase of a cross spectrum.

CITATION LIST

Patent Literature

Patent Literature 1: JP H10-290791A

DISCLOSURE OF INVENTION

Technical Problem

In the above measurement that utilizes the speckle image capturing, it is desirable that the speckle image have a sufficient grain diameter (speckle diameter) for the purpose of analysis. Also, it is desirable that a target region of the speckle image capturing have a sufficient area, when displacement and vibration of the speckle image in the target region are detected.

However, when the target region is expanded, the speckle image is formed by the light reflected and diffused in a wider region, and thus the speckle diameter becomes smaller. Conversely, it is necessary to decrease the target region of the speckle image capturing, in order to increase the speckle diameter. That is, in the technology described in Patent Literature 1 for example, it is difficult to achieve both of ensuring the speckle diameter and expanding the target region of the speckle image capturing.

Thus, the present disclosure proposes a new and improved optical unit, a measurement system, and a measurement method, which are capable of freely setting the target region while ensuring the necessary speckle diameter, in the speckle image capturing that uses the coherent light.

Solution to Problem

According to the present disclosure, there is provided an optical unit that radiates a coherent light such that the coherent light is incident in a target region of speckle image capturing in accordance with a pattern that includes a bright region and a dark region located uniformly in at least one direction in the target region.

Further, according to the present disclosure, there is provided a measurement system including: an optical unit that radiates a coherent light such that the coherent light is incident in a target region in accordance with a pattern that includes a bright region and a dark region located uniformly in at least one direction in the target region; a light reception unit that receives a reflected light of the coherent light in the target region; and an imaging unit that captures an image of a speckle included in the reflected light.

Further, according to the present disclosure, there is provided a measurement method including: radiating a coherent light such that the coherent light is incident in a target region in accordance with a pattern that includes a bright region and a dark region located uniformly in at least one direction in the target region; receiving a reflected light of the coherent light in the target region; and capturing an image of a speckle included in the reflected light.

Advantageous Effects of Invention

As described above, the present disclosure can freely set the target region, while ensuring the necessary speckle diameter in the speckle image capturing that uses the coherent light.

Note that the effects described above are not necessarily limitative. With or in the place of the above effects, there may be achieved any one of the effects described in this specification or other effects that may be grasped from this specification.

BRIEF DESCRIPTION OF DRAWINGS

FIG. 9(a), 9(b), 9(c), 9(d), 9(e), 9(f), 9(g), 9(h) and 9(i) are diagrams for describing first examples of other patterns that can be employed in an embodiment of the present disclosure.

MODE(S) FOR CARRYING OUT THE INVENTION

Figure 1:
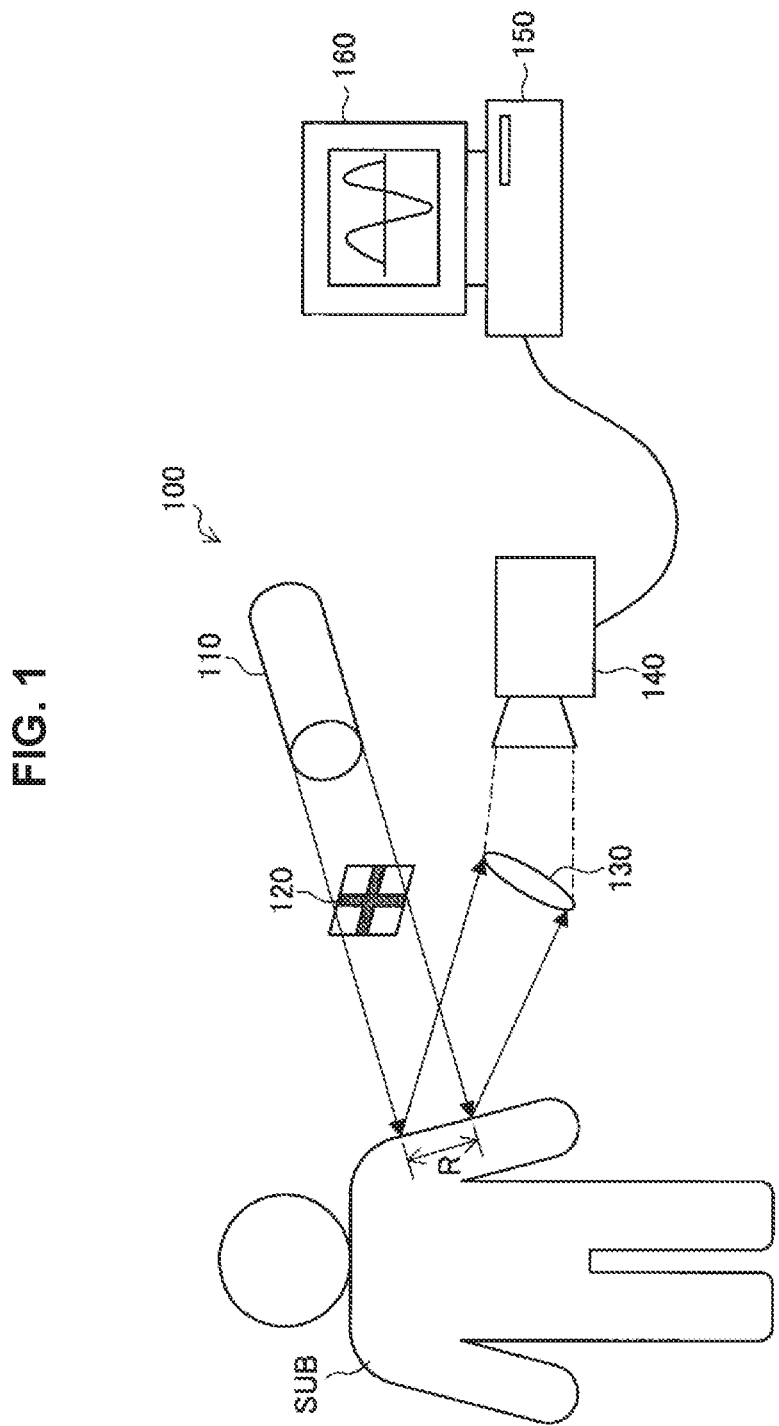
FIG. 1 is a diagram illustrating a schematic configuration of a measurement system according to an embodiment of the present disclosure.

Hereinafter, (a) preferred embodiment(s) of the present disclosure will be described in detail with reference to the appended drawings. In this specification and the appended drawings, structural elements that have substantially the same function and structure are denoted with the same reference numerals, and repeated explanation of these structural elements is omitted.

Note that, description will be made in the following order.
1. System Configuration
2. Relationship Between Size of Target Region and Speckle Diameter
3. Example of Pattern That Includes Slit Bright Region
4. Example of Pattern That Includes Spot Bright Region
5. Example of Other Patterns
6. Hardware Configuration
7. Supplement (1. System Configuration)

FIG. 1 is a diagram illustrating a schematic configuration of a measurement system according to an embodiment of the present disclosure. Referring to FIG. 1, a measurement system 100 includes a light source 110, a filter 120, a light reception unit 130, an imaging unit 140, an analysis unit 150, and an output unit 160. The measurement system 100 performs speckle image capturing in which the imaging unit 140 captures a speckle image formed by coherent light that is radiated from the light source 110 and is reflected and diffused on an epidermis of a subject (user) SUB, and an analysis process for detecting a state or the like of the epidermis of a living body by the analysis unit 150 that analyzes the image obtained by the speckle image capturing, for example.

The light source 110 radiates coherent light on a target region R on the epidermis of the subject SUB. The coherent light is light with a coherent phase, which is suitable to form a speckle image by being reflected on a rough surface such as an epidermis of a living body. More specifically, the coherent light can be laser light, and the light source 110 can be a laser light source device. Note that the present embodiment is satisfactory if the coherent light is coherent to a degree that can form a speckle image with necessary granularity for analysis, and thus the coherent light radiated by the light source 110 is not limited to laser light. As described later, the radiated coherent light is incident on the target region R in accordance with a pattern that includes bright regions and dark regions that are uniformly located in at least one direction in the target region R.

The filter 120 blocks the coherent light radiated toward the target region R from the light source 110 in accordance with a predetermined light blocking pattern. In the example illustrated in the drawing, the coherent light is incident on the target region R in accordance with a predetermined pattern, by this effect of the filter 120. The light blocking pattern fixed by photolithography or the like may be formed in the filter 120, for example. Alternatively, the light blocking pattern may be formed by the filter 120 that includes a liquid crystal element that partially changes transmittance for the coherent light. In this case, the light blocking pattern can be dynamically changed in the filter 120. The light blocking pattern can be changed in accordance with individual variation of the living body of the subject SUB for example. Note that a specific example of the light blocking pattern will be described later.

The light reception unit 130 receives the light reflected on the target region R, of the coherent light radiated from the light source 110 via the filter 120. The coherent light is reflected and diffused on the target region R on the epidermis of the subject SUB, and thus the speckle image is formed in the reflected light. The light reception unit 130 includes various types of optical members, such as a lens for example, which receive the reflected light and guide the reflected light to the imaging unit 140.

The imaging unit 140 includes an image sensor, and generates image data by capturing the speckle image formed in the reflected light received by the light reception unit 130. As described above, the measurement system 100 analyzes the image obtained by the speckle image capturing, and thus the imaging unit 140 may be optimized for the speckle image capturing. For example, the imaging unit 140 may perform the speckle image capturing of the reflected light intermittently at predetermined time intervals, and the generated time-series images may be supplied to the analysis unit 150 sequentially.

The analysis unit 150 analyzes the image obtained by speckle image capturing of the reflected light by the imaging unit 140. For example, the analysis unit 150 may calculate a blood flow rate beneath the epidermis of the target region R, from the displacement of the speckle image between the time-series images. Also, for example, the analysis unit 150 may detect the voice of the subject SUB, from the vibration of the speckle image in the target region R. Note that the analysis target by the analysis unit 150 is not limited to the above example, and can include any target that can be detected by the analysis of the image that includes the speckle. The analysis unit 150 is configured with an information processing apparatus such as a computer that includes various types of processors that operate in accordance with a program, more specifically a central processing unit (CPU), for example. Note that an example of the hardware configuration of the information processing apparatus will be described specifically at the end of the present specification.

The output unit 160 includes an output device such as a display that displays a result of the analysis performed by the analysis unit 150 as an image. The result of the analysis can be expressed by various types of forms, such as a graph, a numerical value, and a text for example, in the image. Also, the output unit 160 may include a speaker that outputs the sound of the result of the analysis, a vibrator that outputs the result of the analysis by a vibration pattern, or the like, in addition to or instead of the display.

The measurement system 100 described above may be implemented in a wearable device worn on the body of the user, for example. Note that the shape of each component of the measurement system 100 is illustrated in FIG. 1, but this shape is schematic for facilitating understanding of the function of each component, and the shape of each component can differ from the one illustrated in the drawing in the implementation. For example, when the measurement system 100 is implemented in the wearable device, the light source 110, the filter 120, the light reception unit 130, the imaging unit 140, the analysis unit 150, and the output unit 160 each have a compact shape and are integrated in a housing of the wearable device.

A specific example of the wearable device in which the measurement system 100 is implemented as described above includes a wristwear worn on a wrist part of the user, a neckwear (or a pendant) worn on a neck part of the user, or the like. For example, the wristwear can measure a blood flow rate of a blood vessel of the wrist part by the measurement system 100. In this case, the target region R of the speckle image capturing includes a region on the epidermis corresponding to the blood vessel of the wrist part. Also, for example, the neckwear can detect voice of the user from the vibration of a skin of a throat part by the measurement system 100. In this case, the target region R of the speckle image capturing includes a region on an epidermis that gives instruction by the voice of the user.

Also, as another example, the measurement system 100 may be distributedly implemented in the wearable device worn on the body of the user and another device that communicates with the wearable device. In this case, the light source 110, the filter 120, the light reception unit 130, and the imaging unit 140 can be implemented in the wearable device, and the analysis unit 150 and the output unit 160 can be implemented in the other device, for example. The other device may be a mobile device such as a smartphone and a tablet carried by the user, and may be a fixed device such as a personal computer, for example. Also, the other device may include a server on a network in which an analysis unit 150 is implemented, and a mobile device or a fixed device that receives an analysis result from the server and outputs the analysis result to the user, for example.

The measurement system 100 may be implemented in a device that is installed fixedly, as yet another example. In this device, for example, the light source 110, the filter 120, and the light reception unit 130 are arranged to radiate the coherent light on a body part (for example, wrist, etc.) of the user located at a predetermined position and to receive the reflected light. Unlike the above example of the wearable device, the user takes out the device (or moves to the device) as necessary to perform the measurement. Note that the analysis unit 150 and the output unit 160 may also be implemented in a separate device from other components when the measurement system 100 is implemented in the device that is fixedly installed, for example.

Also, in the measurement system 100 described above, the light source 110 and the filter 120 may be handled as a merged optical unit, and may be each handled as a separate optical unit. For example, the filter 120 can be an independent member that is replaceable as appropriate in accordance with a necessary pattern of the coherent light.

Also, the measurement system 100 is needless to include the filter 120 necessarily. For example, the filter 120 is needless to be provided necessarily, when the light source 110 can radiate the coherent light in accordance with a predetermined pattern. More specifically, when the pattern includes spot bright regions scattered as in an example described later, the light source 110 may be implemented with a cluster of point light sources corresponding to respective spots, for example. When the light source 110 radiates the coherent light in accordance with a predetermined pattern and the filter 120 is not provided, the diffraction of the coherent light that occurs when the coherent light passes through the filter 120 can be eliminated. Also, even when the filter 120 is provided, the diffraction of the coherent light that occurs when the coherent light passes through the filter 120 can be reduced, by making the pattern of the coherent light radiated from the light source 110 correspond to the light blocking pattern. Also, as another example, the light source 110 may include an optical element, such as a lens, and be capable of radiating the coherent light in such a manner that the coherent light is incident on the target region in accordance with a predetermined pattern by transformation or interference after the radiation.

As described above, in the present embodiment, the light source 110 and the filter 120 or one of the light source 110 or the filter 120 can function as an optical unit that radiates the coherent light in such a manner that the coherent light is incident on the target region of the speckle image capturing in accordance with a predetermined pattern. Note that the bright regions and the dark regions included in a predetermined pattern may be distinctly differentiated like light blocking parts and transmission parts in the light blocking pattern of the filter 120 described later, for example. Alternatively, the intensity of the coherent light may change between the bright regions and the dark regions in a phased manner.

(2. Relationship Between Size of Target Region and Speckle Diameter)

In the following, a relationship between the size of the target region R of the speckle image capturing performed by the above measurement system 100 and a grain diameter (speckle diameter) of the speckle image formed by the coherent light radiated in the target region R will be described with reference to FIGS. 2 to 4. Note that, in the description that refers to FIGS. 2 to 4, the light blocking of the coherent light by the filter 120 included in the measurement system 100 is not considered, and the coherent light is assumed to be evenly radiated on the entire target region R by the light source 110.

Figure 2:
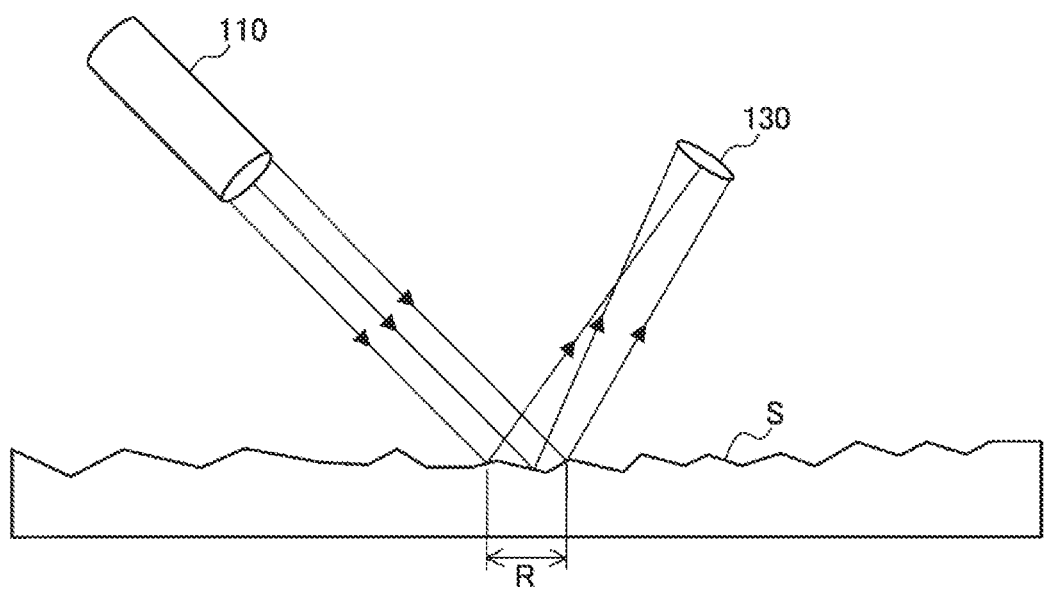
FIG. 2 is a diagram conceptually illustrating a relationship between coherent light radiated from a light source and a speckle image.

FIG. 2 is a diagram conceptually illustrating a relationship between the coherent light radiated from the light source and the speckle image. As described already, in the measurement system 100, the coherent light radiated from the light source 110 is reflected and diffused by the epidermis of the subject SUB, and the light reception unit 130 receives the reflected light, and thereby the speckle image is observed. Note that, in the below description, the epidermis of the subject SUB in the measurement system 100 will be generalized and described as a rough surface S. Also, a region on the rough surface S on which the light from the light source 110 is radiated when there is no the filter 120 is set as the target region R of the speckle image capturing.

Figure 3:
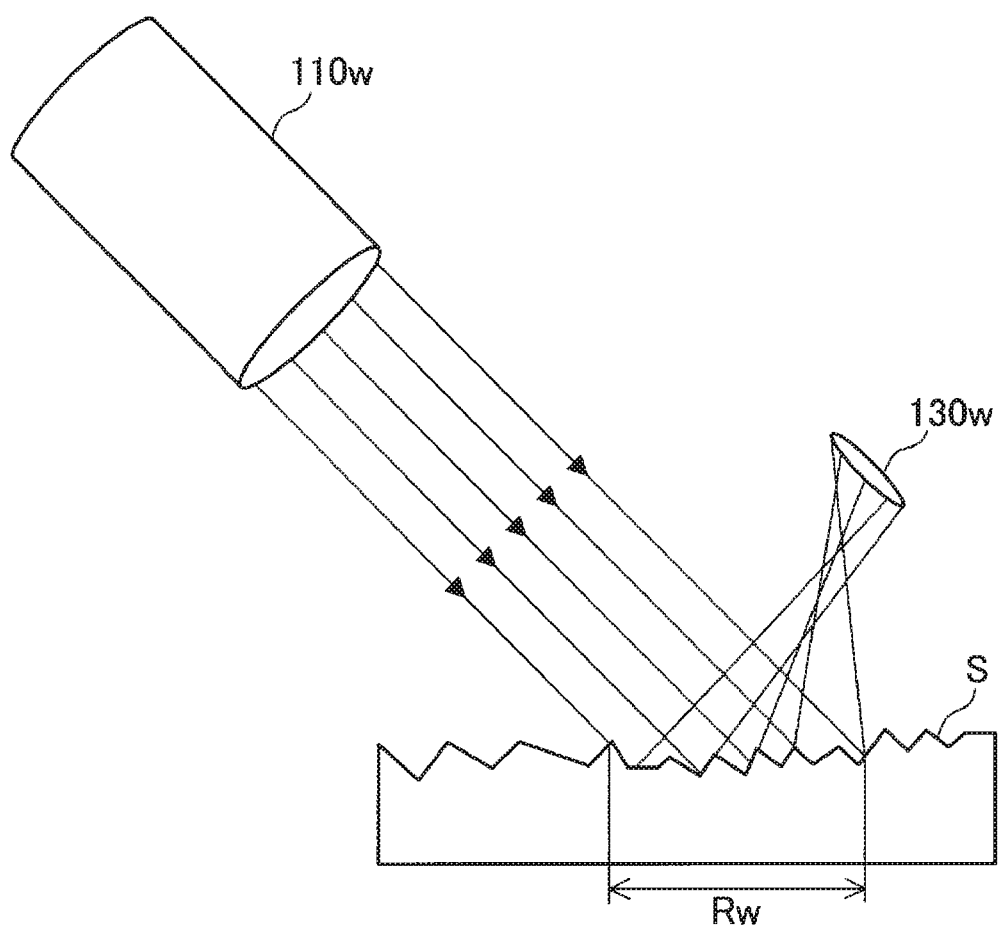
FIG. 3 is a diagram illustrating a case in which a target region is expanded in an example illustrated in FIG. 2.

FIG. 3 is a diagram illustrating a case in which the target region is expanded in the example illustrated in FIG. 2. In the example illustrated in FIG. 3, a light source 110w radiates the coherent light on a target region Rw on the rough surface S, which is wider than the target region R illustrated in FIG. 2. In this case, a speckle image of a larger size than the example illustrated in FIG. 2 is observed in a light reception unit 130w.

Figure 4:
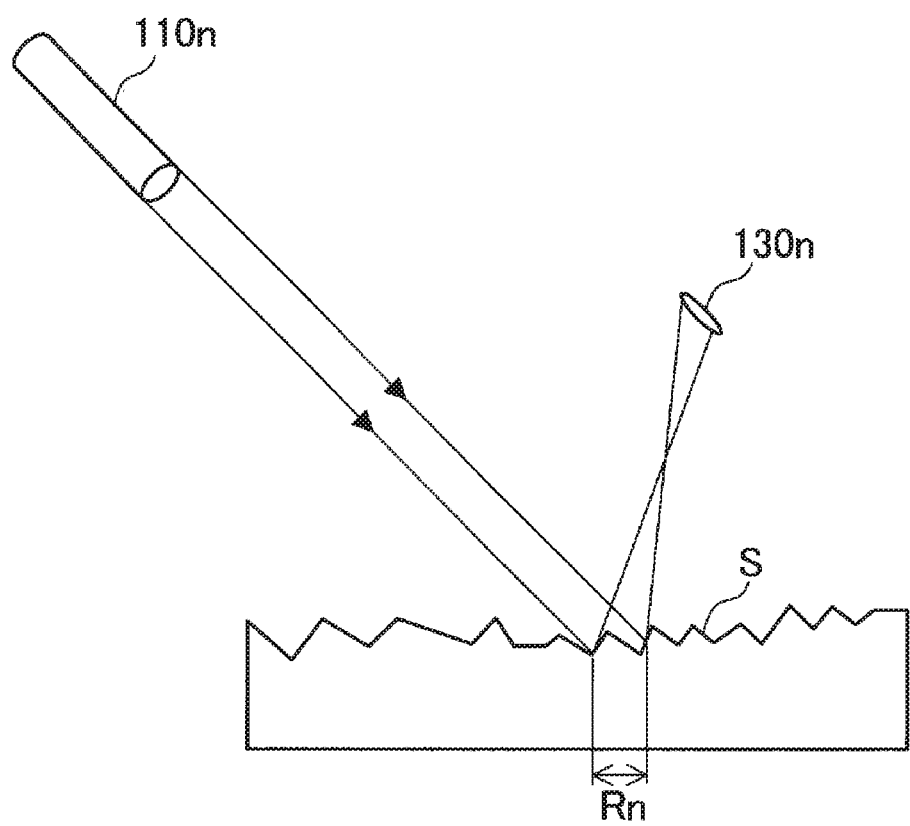
FIG. 4 is a diagram illustrating a case in which a target region is decreased in an example illustrated in FIG. 2.

FIG. 4 is a diagram illustrating a case in which the target region is decreased in the example illustrated in FIG. 2. In the example illustrated in FIG. 4, a light source 110n radiates the coherent light on a target region Rn on the rough surface S, which is narrower than the target region R illustrated in FIG. 2. In this case, a speckle image of a smaller size than the example illustrated in FIG. 2 is observed in a light reception unit 130n.

Here, for example, matching of a common part of the speckle image is needed to detect the displacement and vibration of the speckle images captured in temporal sequence by the imaging unit 140 that captures an image of the reflected light received by the light reception unit 130. In order to execute this matching unfailingly, it is conceived that the target region is expanded as in the example illustrated in FIG. 3, and even when large displacement or vibration occurs in the speckle image, the region of the speckle image that is common before and after the displacement or the movement is made inside the target region. Note that such displacement and vibration are generated by a motion of the speckle image itself due to change of the state of the rough surface S, and can occur when the rough surface S itself moves or when the measurement system 100 moves.

However, when the coherent light is radiated on the wider target region Rw by the light source 110w, a larger amount of light is reflected and diffused to interfere with each other, and therefore the grain diameter (speckle diameter) of the formed speckle image becomes smaller as in the example of FIG. 3, for example. When the speckle diameter is small, the accuracy of the matching of the speckle image decreases, and thus erroneous detection (noise) increases in the detection of the displacement and the vibration, for example.

On the other hand, when the target region is decreased as in the example illustrated in FIG. 4, the light that is reflected and diffused to interfere with each other is reduced, and therefore the grain diameter (speckle diameter) of the formed speckle image can be kept large as in the example of FIG. 4, for example. When the speckle diameter is large, the accuracy of the matching of the speckle image is improved, and thus the erroneous detection (noise) can be reduced in the detection of the displacement and the vibration, for example. However, when the coherent light is radiated on the narrower target region Rn by the light source 110n, it is highly possible that the speckle image before and after the displacement and the vibration does not include the common part, for example.

As described above, if the light source 110 evenly radiate the coherent light on the entire target region R in the measurement system 100 according to the present embodiment, a situation occurs in which it is difficult to achieve both of the ensuring of the speckle diameter and the expansion of the target region of the speckle image capturing.

Thus, in the measurement system 100 according to the present embodiment, the target region is enabled to be expanded while ensuring a necessary speckle diameter, by applying a predetermined light blocking pattern by the filter 120 to the coherent light radiated in the target region R from the light source 110. In the following, the arrangement of the filter 120 that enables the above or the light blocking pattern itself will be described further. Note that application of the pattern may be achieved by the configuration of the light source 110 itself, and in that case the filter 120 is needless to be provided as described already.

(3. Example of Pattern That Includes Slit Bright Region)

Figure 5:
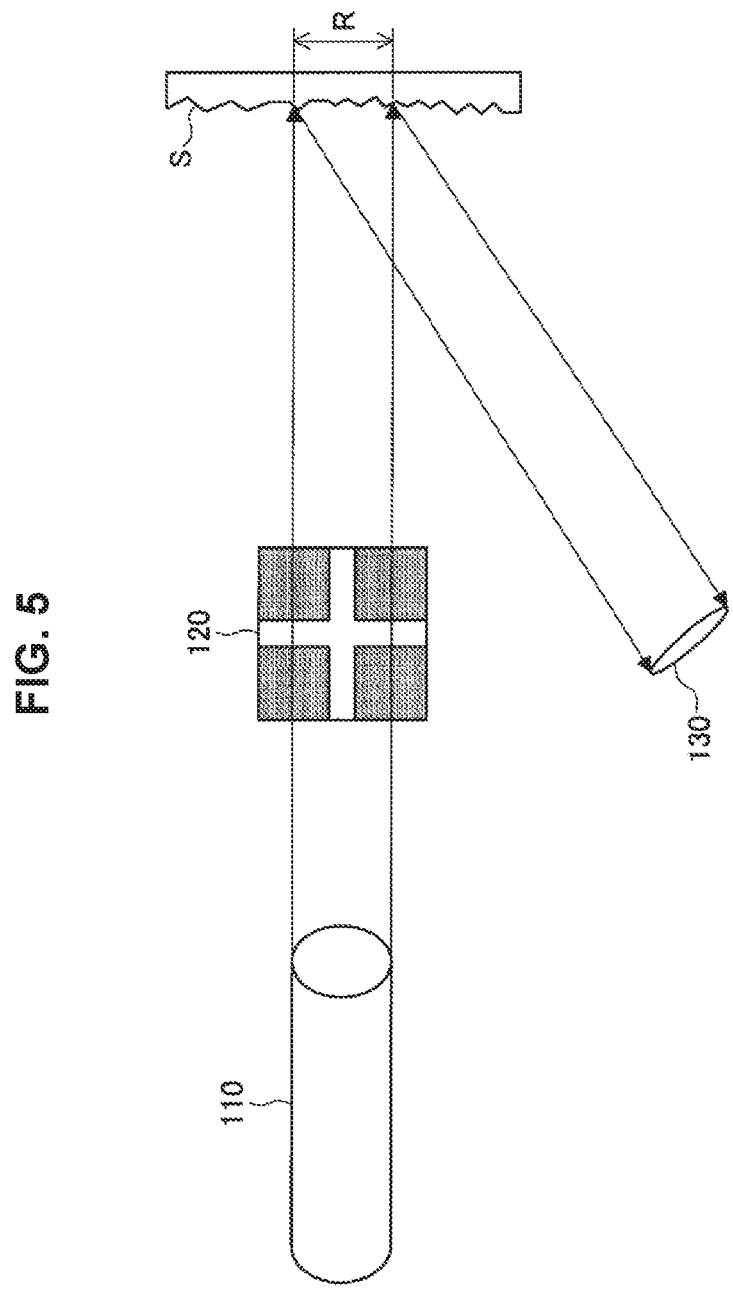
FIG. 5 is a diagram conceptually illustrating an example of a configuration for causing coherent light to be incident on a target region of speckle image capturing in accordance with a pattern in an embodiment of the present disclosure.

FIG. 5 is a diagram conceptually illustrating an example of the configuration for causing the coherent light to be incident in accordance with the pattern in the target region of the speckle image capturing in an embodiment of the present disclosure. In the example illustrated in the drawing, in the measurement system 100, the filter 120 blocks the coherent light that is radiated in the target region R on the rough surface S from the light source 110, in accordance with a pattern that includes a cross-shaped slit transmission part. The coherent light that passes through the filter 120 is incident and reflected and diffused in a substantially cross-shaped slit bright region that corresponds to the transmission part of the light blocking pattern in the target region R, and the light reception unit 130 receives the reflected light, and thereby the speckle image is observed.

Figure 6:
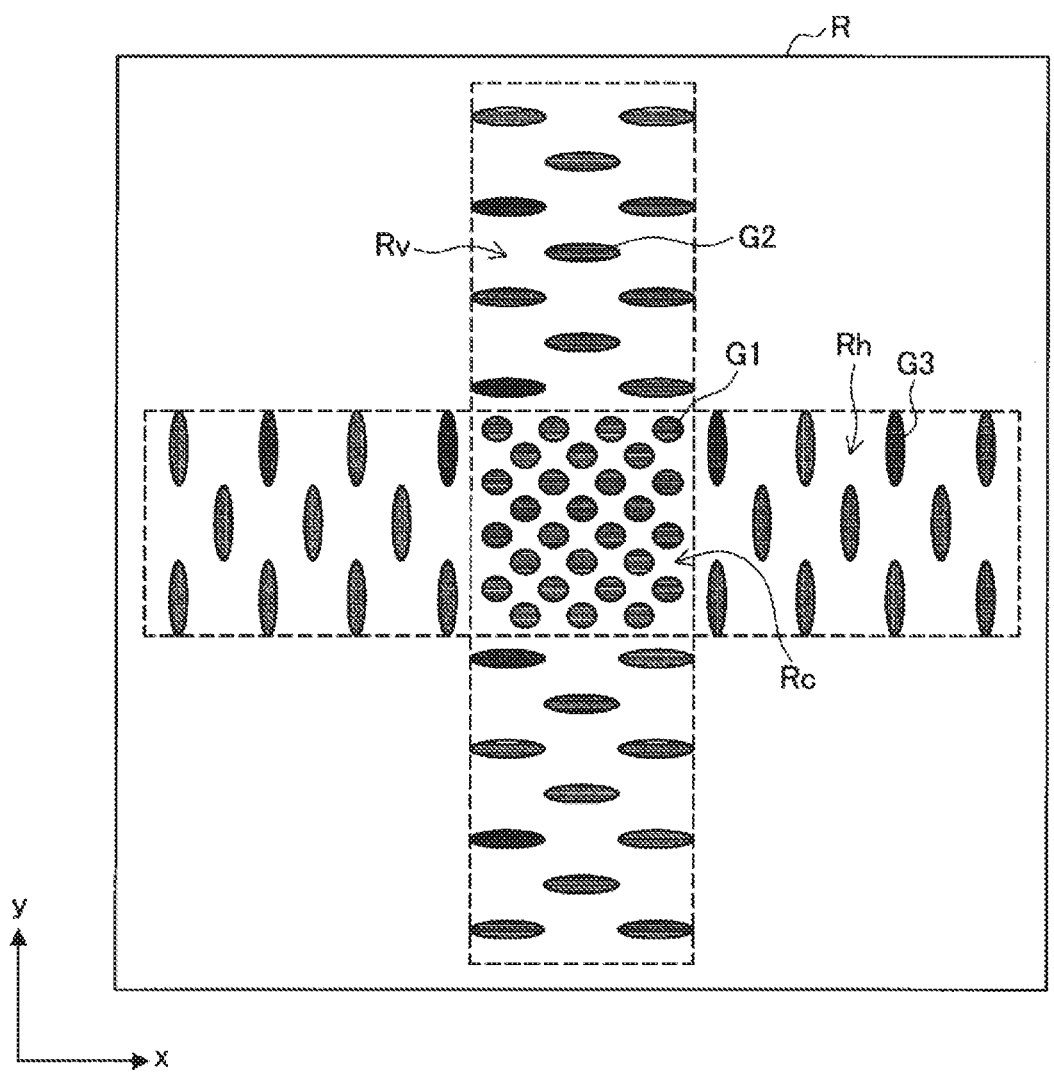
FIG. 6 is a diagram conceptually illustrating a speckle image observed in an example illustrated in FIG. 5.

FIG. 6 is a diagram conceptually illustrating the speckle image observed in the example illustrated in FIG. 5. The speckle image observed in the example illustrated in FIG. 5 can be observed in the substantially cross-shaped bright region illustrated in FIG. 6, for example. In the example illustrated in the drawing, three types of speckle grains G1 to G3 are included in this speckle image. Note that, in order to describe the relationship between slit directions and the shape of the speckle grains, x axis in the left-right direction and y axis in the vertical direction are illustrated in the drawing.

In the example illustrated in the drawing, the speckle grain G1 is observed in a bright region Rc at an intersecting part at the center of a cross shape. The reflected light of the coherent light in this region interferes with the coherent light that is incident and reflected and diffused in the bright regions adjacent in four directions in the x axis direction and the y axis direction, and therefore the grain diameter (speckle diameter) of the speckle grain G1 becomes smaller to the same degree as a case in which the coherent light is radiated evenly on the entire target region R, for example.

On the other hand, in the example illustrated in the drawing, the speckle grain G2 is observed in a bright region Rh of an arm part extending in the x axis direction of the cross shape. The reflected light of the coherent light in the bright region Rh interferes with the coherent light that is incident and reflected and diffused in the bright regions (the bright region Rh or the bright region Rc) adjacent in the x axis direction. On the other hand, the coherent light is not incident (or weaker coherent light than the bright regions is incident) in the dark regions adjacent to the bright region Rh in the y axis direction (that is, the dark regions that are positioned above and below the region Rh in the drawing), and thus the coherent light reflected and diffused in these dark regions does not interfere with the reflected light of the coherent light in the bright region Rh (or the interference is small sufficiently), and thus the grain diameter (speckle diameter) of the speckle grain G2 is kept large in the y axis direction particularly.

In the same way, in the example illustrated in the drawing, a speckle grain G3 is observed in a bright region Rv of an arm part extending in the y axis direction of the cross shape. The reflected light of the coherent light in the bright region Rv interferes with the coherent light reflected and diffused in the bright regions (the bright region Rv, or the bright region Rc) adjacent in the y axis direction. On the other hand, the coherent light is not incident (or the weaker coherent light than the bright region is incident) in the dark regions adjacent to the bright region Rv in the x axis direction (that is, the dark regions that are positioned at the left and right of the region Rv in the drawing), and thus the coherent light reflected and diffused in these dark regions does not interfere with the reflected light of the coherent light in the bright region Rv (or the interference is small sufficiently), and thus the grain diameter (speckle diameter) of the speckle grain G3 is kept large in the x axis direction particularly.

In the example illustrated in FIG. 6 in the above, the speckle diameter is kept large in at least one direction in the bright regions Rh, Rv, and thus the displacement and the vibration of the speckle image can be detected accurately, for example. Further, the bright region Rh covers the substantially entire target region R in the x axis direction, and in the same way the bright region Rv covers the substantially entire target region R in the y axis direction. Thus, when the size of the target region R is set sufficiently large, it is highly possible that the displacement and the vibration in the x axis direction of the speckle image is detected by the matching of the speckle image in the bright region Rh, and it is highly possible that the displacement and the vibration in the y axis direction of the speckle image is detected by the matching of the speckle image in the bright region Rv.

As a result, in the measurement system 100 in which the coherent light is incident in the target region R in accordance with the pattern like the example illustrated in FIGS. 5 and 6, the expansion of the target region of the speckle image capturing is achieved, while ensuring the necessary speckle diameter in at least one direction.

(4. Example of Pattern That Includes Spot Bright Region)

Figure 7:
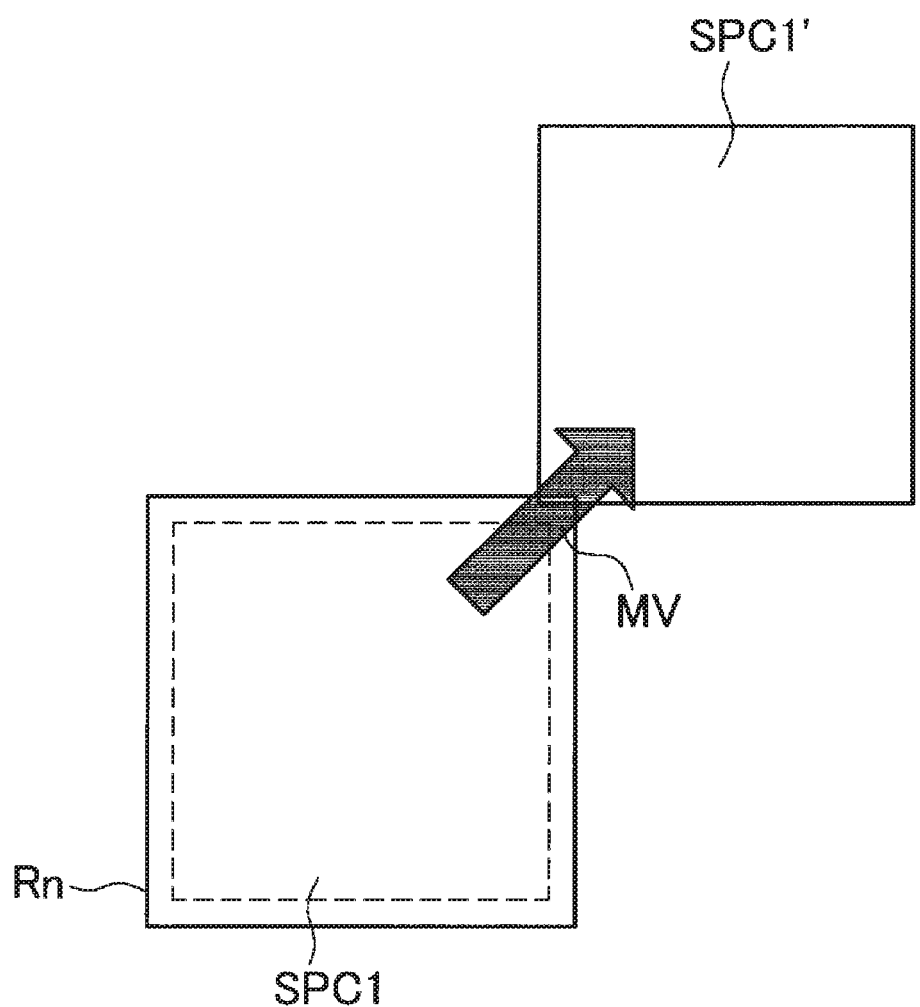
FIG. 7 is a diagram for further describing a case in which a target region of speckle image capturing is decreased.

FIG. 7 is a diagram for describing again that the matching of the speckle image can become difficult due to the displacement or the vibration of the speckle image, when the target region of the speckle image capturing is decreased as in the example illustrated in FIG. 4 for example, before describing an example of a pattern that includes spot bright regions. In the example illustrated in FIG. 7, the speckle image SPC1 observed in the target region Rn comes off from the target region Rn by the displacement indicated by a motion vector MV (unobserved speckle image SPC1'). In this case, in the speckle image observed by the target region Rn, a common part is not included before and after the displacement, and it is difficult to detect the displacement by the matching. However, when the target region Rn is expanded, the speckle diameter becomes smaller, and the erroneous detection (noise) increases in the detection of the displacement and the vibration for example, as described already.

Figure 8:
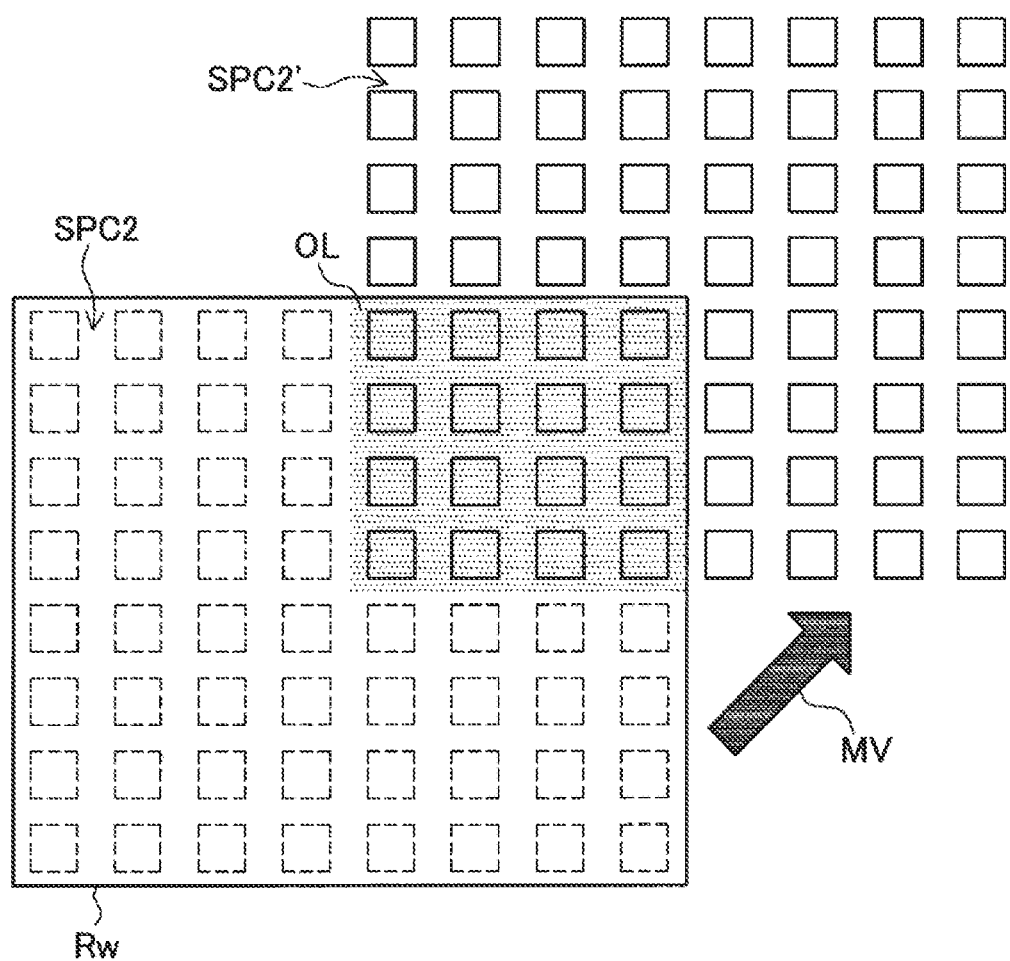
FIG. 8 is a diagram for describing an effect when coherent light is caused to be incident in accordance with a pattern that includes spot bright regions in an embodiment of the present disclosure.

FIG. 8 is a diagram for describing an effect obtained when the coherent light is caused to be incident in the target region of the speckle image capturing in accordance with a pattern that includes the spot bright regions in an embodiment of the present disclosure, in comparison with the example illustrated in FIG. 7. Note that the x axis in the left-right direction and the y axis in the vertical direction are illustrated in the drawing, in order to describe the relationship between the location of the spot and the shape of the speckle grain, in the same way as the example of FIG. 6.

In the example illustrated in the drawing, in the measurement system 100, the filter 120 blocks the coherent light that is radiated in the target region R on the rough surface S from the light source 110, in accordance with the light blocking pattern that includes rectangular spot transmission parts arrayed at regular intervals in each of the x axis direction and the y axis direction. Note that the configuration for applying the light blocking pattern to the coherent light is the same as the example described with reference to FIG. 5 in the above, and thus duplicate description will be omitted. Thereby, in the example illustrated in the drawing, the coherent light that passes through the filter 120 is incident and reflected and diffused in the spot bright regions corresponding to the transmission parts of the light blocking pattern on the target region R, and the light reception unit 130 attends an lecture of the reflected light, and thereby the speckle image is observed.

Here, the target region Rw illustrated in FIG. 8 is a region that is expanded more than the target region R illustrated in FIG. 7. Thus, for example, when a speckle image SPC2 observed in the target region Rw becomes a speckle image SPC2' by the displacement indicated by the same motion vector MV as that illustrated in FIG. 7, an overlap region OL is generated between the speckle image SPC2 and the speckle image SPC2', and the displacement of the speckle image can be detected by matching the speckle image in this region.

For example, as opposed to a case in which the target region is expanded simply as in the example illustrated in FIG. 3, in the example illustrated in FIG. 8, the density of the coherent light radiated in the target region Rw is restricted by applying the pattern, while the target region is expanded, and the interference of the reflected and diffused light occurs excessively, and thereby the speckle diameter is prevented from becoming small. As a result, in the measurement system 100 in which the coherent light is incident in the target region R in accordance with the pattern like the example illustrated in FIG. 8, the expansion of the target region of the speckle image capturing is achieved, while ensuring the necessary speckle diameter.

Note that the description referring to the above FIG. 7 has described, for simplicity, an example in which it is possible that the region of the speckle image does not overlap completely between the images that are continuous in the temporal sequence, but an example to which the present embodiment is applicable is not limited to this example. For example, even when the region of the speckle image overlaps to a certain degree between the images that are continuous in the temporal sequence, the images that include the common part of the speckle image increases in number, and thereby the robustness of the analysis can be improved.

More specifically, for example, by smoothing the motion of the speckle image detected by the matching of the images of the respective frames for example, the noise included in the detection result is reduced, and the detection of the displacement or the vibration can be performed more robustly in a case in which the common part of the speckle image is included in three frames or more frames, than in a case in which the common part of the speckle image is included only in the images of two frames that are continuous in the temporal sequence. In the example described with reference to FIG. 8 in the above, the target region Rw of the speckle image capturing is set wide, and thereby the common part of the speckle image is included in more frames of the images that are continuous in the temporal sequence, and the robustness of detection can be improved.

(5. Example of Other Patterns)

FIG. 9(*a*), 9(*b*), 9(*c*), 9(*d*), 9(*e*), 9(*f*), 9(*q*), 9(*h*) and 9(*i*) are diagrams for describing first examples of other patterns that can be employed in an embodiment of the present disclosure. In the following, each of the patterns illustrated in FIGS. 9(*a*), 9(*b*), 9(*c*), 9(*d*), 9(*e*), 9(*f*), 9(*g*), 9(*h*) and 9(*i*) will be described. Note that, in the examples illustrated in the drawing, the patterns (for example, formed by the above filter 120) are rectangular as a whole, but the embodiment of the present disclosure is not limited to this example, and the entire shape of the pattern can be various shapes, such as a circle and a hexagon. Also, when the light source 110 can radiate the coherent light in accordance with the pattern (more specifically, when the light source 110 is configured with a cluster of point light sources corresponding to scattered spots, for example), the outer shape of the pattern is needless to be stipulated particularly.

The FIGS. 9(*a*), 9(*b*) and 9(*c*) are examples in which the pattern is configured with slits in the vertical direction or the lateral direction in the rectangle. In FIG. 9(*a*), the pattern is configured with a plurality of slits that each extend in the vertical and lateral two directions. In this case, in the same way as the example illustrated in FIG. 6 in the above, the displacement and the vibration of the speckle image can be detected accurately in each of the vertical direction and the lateral direction, and the slits cover the entire area of the pattern, and therefore the displacement and the vibration can be detected in the entire target region. On the other hand, in FIG. 9(*b*) and FIG. 9(*c*), the pattern is configured with a plurality of slits that extend in one of the vertical and lateral directions of the rectangle. In this case, the displacement and the vibration of the speckle image can be detected accurately in the entire target region in one of the vertical direction and the lateral direction. For example, when the direction of the displacement or the vibration of the speckle image is predicted, a pattern such as the above FIG. 9(*b*) or FIG. 9(*c*) can be useful.

The FIGS. 9(*d*), 9(*e*) and 9(*f*) are examples in which the pattern is configured with slits in oblique directions in the rectangle. In FIG. 9(*d*), the pattern is configured with a single slit that extends in two oblique directions. In this example, the location of the slit in the example illustrated in FIG. 6 in the above is rotated by 45° with respect to a center. In FIG. 9(*e*), the pattern is configured with a single slit that extends in the vertical, lateral, and oblique four directions. This case can detect the displacement and the vibration of the speckle image in more directions, and thus can be useful when the direction of the displacement or the vibration of the speckle image is not predicted, for example. The FIG. 9(*f*) is a pattern that locates slits that extend in vertical, lateral, and oblique four directions in the same way as FIG. 9(*e*), in which the slits in the respective directions are divided into two to prevent the interference from becoming large at the intersecting part of the slits and making the speckle diameter smaller.

The FIG. 9(*g*) is an example in which the slits in the vertical and lateral directions are divided to prevent the interference at the intersecting part in the same way as the above FIG. 9(*f*), and additionally the axes of the slits are shifted in the respective directions, in order to expand the area in which the displacement and the vibration are detectable. The FIG. 9(*h*) is provided with a plurality of slit patterns of FIG. 9(*g*) that are made smaller. The FIG. 9(*i*) is an example in which fine slits in the vertical, lateral, and oblique directions are located at random.

When the pattern is configured with the slits as in the examples described with reference to FIGS. 9(*a*), 9(*b*), 9(*c*), 9(*d*), 9(*e*), 9(*f*), 9(*g*), 9(*h*) and 9(*i*) in the above, the interference of the reflected and diffused coherent light is moderately reduced in the direction orthogonal to the slit, as described with reference to FIG. 6 in the above for example, and thus the speckle diameter can be kept large as compared with a case that does not apply the pattern. Also, the speckle image can be observed continuously in the direction in which the slit extends, and thus the direction of the displacement and the vibration of the speckle image generated in the direction along the slit can be detected particularly accurately. The area in which the displacement and the vibration of the speckle image are detectable can be expanded by locating a plurality of slits that extend in a common direction. Also, the displacement and the vibration of the speckle image can be detected in each direction by locating the slits that extend in a plurality of directions.

Also, in the above examples FIGS. 9(*a*), 9(*b*), 9(*c*), 9(*d*), 9(*e*), 9(*f*), 9(*q*), 9(*h*) and 9(*i*) the slits are uniformly located in at least one direction in the pattern. That is, in the examples FIGS. 9(*a*), 9(*b*) and 9(*c*) for example, the slits of the same width are located evenly in the vertical direction or the lateral direction. Also, in the examples FIGS. 9(*d*), 9(*e*), 9(*f*) and 9(*g*) the slits of the same width are located with point symmetry with respect to the center of the pattern. In the examples FIG. 9(*h*) and FIG. 9(*i*), the slits of the same width are located in an almost same number in each of the vertical, lateral, and oblique directions. As described above, by uniformly locating the slits in the pattern in at least one direction, the coherent light is incident in the target region in accordance with the pattern of the bright regions and the dark regions located uniformly in at least one direction. More specifically, the coherent light may be incident only in the bright regions and be blocked in the dark regions. Alternatively, it may be such that more intense coherent light is incident in the bright regions and weaker coherent light is incident in the dark regions. Thereby, the speckle image can be observed uniformly in at least one direction in the target region, in the same way as a case in which the coherent light is incident in the entire target region, for example. The coherent light is incident in accordance with the pattern, and thereby the speckle diameter can be kept large, as described already.

Figure 10J:
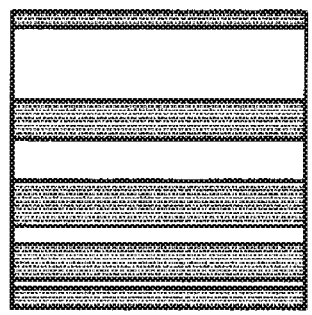
FIGS. 10(j), 10(k) and 10(l) are diagrams for describing second examples of other patterns that can be employed in an embodiment of the present disclosure.
Figure 10K:
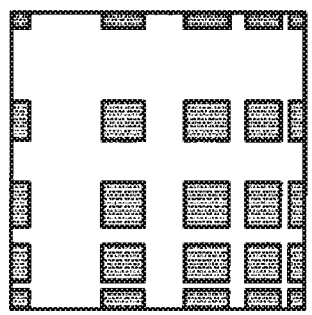
Figure 10L:
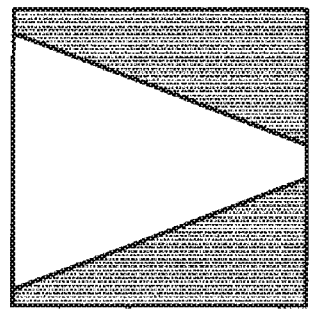

FIGS. 10(*i*), 10(*k*) and 10(*l*) are diagrams for describing second examples of other patterns that can be employed in an embodiment of the present disclosure. In the following, each of the patterns illustrated in FIGS. 10(*i*), 10(*k*) and 10(*l*) will be described. Note that, in the same way as the examples described with reference to FIGS. 9(*a*), 9(*b*), 9(*c*), 9(*d*), 9(*e*), 9(*f*), 9(*q*), 9(*h*) and 9(*i*) in the above, the entire shape of the pattern is not limited to a rectangle, and the outer shape of the pattern is needless to be stipulated particularly.

In FIG. 10(*j*), the pattern is configured with slits that extend in the lateral direction in the rectangle. As a difference from the example FIG. 9(*c*), in FIG. 10(*j*), the width of the slit becomes narrower on the lower side in the drawing, and becomes wider on the upper side (that is, the width of each slit are different). For example, the configuration of this pattern can be useful, when the displacement of the speckle image is to be detected from the lower side to the upper side particularly. Although not illustrated in the drawings, slits that extend in the vertical direction in the rectangle can have a similar configuration. In FIG. 10(*k*), slits whose widths change in the same way as the above FIG. 10(*j*) are located in both of the vertical and lateral directions.

Also in FIG. 10(*l*), the pattern is configured with a slit bright region that extends in the lateral direction in the rectangle. As a difference from the above example FIG. 10(*j*), in FIG. 10(*l*), the width of the slit becomes wider on the left side in the drawing, and becomes narrower on the right side (that is, the width changes in the single slit). For example, the configuration of this pattern can be useful, when the displacement of the speckle image is to be detected from the right side to the left side particularly. Although not illustrated in the drawings, a slit that extends in the vertical direction in the rectangle can have a similar configuration. Also, a similar configuration can be employed when a plurality of slits that extend in a common direction are located.

In the examples described with reference to FIGS. 10(*j*), 10(*k*) and 10(*l*) in the above, the pattern is configured with the slit bright regions, and thus the target region of the observation is expanded while the speckle diameter is kept large, and the direction of the displacement and the vibration of the speckle image generated in the direction along the slits can be detected accurately particularly. Also, in the above examples FIGS. 10(*j*), 10(*k*) and 10(*l*), the bright regions are formed with the asymmetrically shaped slits in the same direction, and thus the displacement of the speckle image can be detected at higher accuracy, when asymmetric displacement in a specific direction (more specifically, displacement limited to the vertical direction from the lower side to the upper side) is to be detected, for example.

Figure 11O:
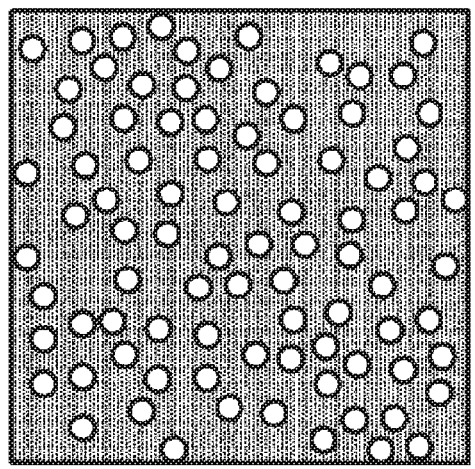
FIGS. 11(m), 11(n) and 11(o) diagrams for describing third examples of other patterns that can be employed in an embodiment of the present disclosure.
Figure 11N:
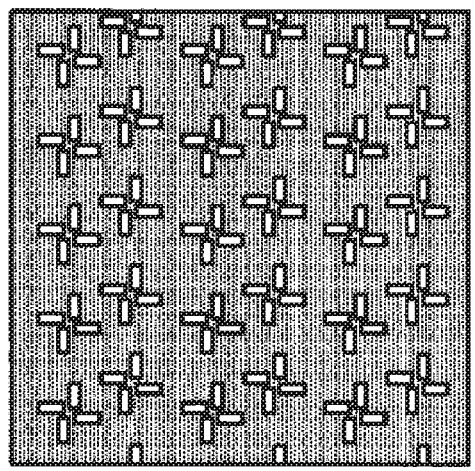
Figure 11M:
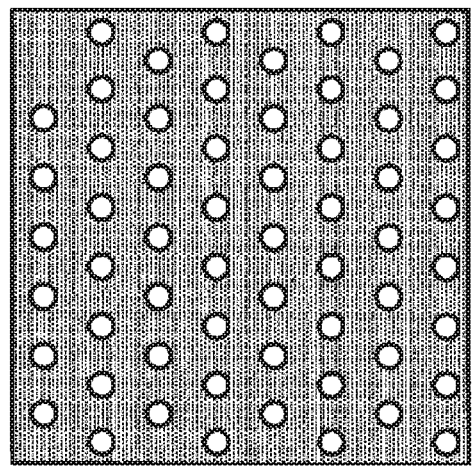

FIGS. 11(*m*), 11(*n*) and 11(*o*) are diagrams for describing third examples of other patterns that can be employed in an embodiment of the present disclosure. In the following, each of the patterns illustrated in FIGS. 11(*m*), 11(*n*) and 11(*o*) will be described. Note that, in the same way as the examples described with reference to FIGS. 9(*a*), 9(*b*), 9(*c*), 9(*d*), 9(*e*), 9(*f*), 9(*q*), 9(*h*) and 9(*i*) in the above, the entire shape of the pattern is not limited to a rectangle, and the outer shape of the pattern is needless to be stipulated particularly.

In the examples illustrated in the drawing, the pattern includes scattered spot bright regions, in the same way as the examples described with reference to FIG. 8 in the above. As opposed to a case of the slit, the interference of the reflected and diffused coherent light can be moderately reduced omnidirectionally, by configuring the bright regions with the scattered spots. In the example illustrated in FIG. 11(*m*), the pattern is configured with circular spot bright regions which are arrayed at regular intervals. Note that the shapes of the bright regions may be a circle like the example FIG. 11(*m*), and may be an ellipse, and may be a polygon such as a rectangle, a triangle, and a hexagon illustrated in the examples of FIG. 8. Also, as illustrated by the example FIG. 11(*m*), even when the bright regions are arrayed at regular intervals in the pattern, the position of each bright region is needless to be aligned in the direction such as the vertical and lateral direction necessarily. In the example illustrated in FIG. 11(*n*), the spots that configure the bright regions have a shape of a combination of slits in the vertical direction and the lateral direction, in the same way as the example of FIG. 9(*h*). In the example illustrated in FIG. 11(*o*), the same circular spot bright regions as the example FIG. 11(*m*) are located at random.

In the examples FIGS. 11(*m*), 11(*n*) and 11(*o*) described in the above, the spots are located uniformly in the incident pattern of the coherent light. In the examples FIG. 11(*m*) and FIG. 11(*n*), the spots are located at regular intervals, and the locations of the spots are uniform in each direction. Also, in the example FIG. 11(*o*) as well, the locations of the spots are assumed to be uniform as a whole, if the range of the intervals between the spots set at random is set appropriately (that is, within a range that is not too large relative to the size of the pattern). As described above, by locating the spot bright regions uniformly in the pattern, the coherent light is incident in the target region in accordance with the pattern of the bright regions and the dark regions located uniformly. Thereby, the speckle image can be observed uniformly in the target region, in the same way as a case in which the coherent light is incident in the entire target region for example. The coherent light is incident in accordance with the pattern, and thereby the speckle diameter can be kept large, as described already.

(6. Hardware Configuration)

Next, with reference to FIG. 12, an exemplary hardware configuration of the information processing apparatus in the embodiment of the present disclosure will be described. FIG. 12 is a block diagram illustrating an exemplary hardware configuration of the information processing apparatus in the embodiment of the present disclosure. An information processing apparatus 900 illustrated in the drawing can configure the analysis unit 150 (which may include the output unit 160) included in the measurement system 100 in the above embodiment, for example.

The information processing apparatus 900 includes a central processing unit (CPU) 901, read only memory (ROM) 903, and random access memory (RAM) 905. In addition, the information processing apparatus 900 may include a host bus 907, a bridge 909, an external bus 911, an interface 913, an input apparatus 915, an output apparatus 917, a storage apparatus 919, a drive 921, a connection port 923, and a communication apparatus 925. The information processing apparatus 900 may include a processing circuit such as a digital signal processor (DSP), an application-specific integrated circuit (ASIC), or a field-programmable gate array (FPGA), alternatively or in addition to the CPU 901.

The CPU 901 serves as an arithmetic processing apparatus and a control apparatus, and controls the overall operation or a part of the operation of the information processing apparatus 900 according to various programs recorded in the ROM 903, the RAM 905, the storage apparatus 919, or a removable recording medium 927. The ROM 903 stores programs, operation parameters, and the like used by the CPU 901. The RAM 905 transiently stores programs used when the CPU 901 is executed, and various parameters that change as appropriate when executing such programs. The CPU 901, the ROM 903, and the RAM 905 are connected with each other via the host bus 907 configured from an internal bus such as a CPU bus or the like. The host bus 907 is connected to the external bus 911 such as a Peripheral Component Interconnect/Interface (PCI) bus via the bridge 909.

The input apparatus 915 is a device operated by a user such as a mouse, a keyboard, a touch panel, a button, a switch, and a lever. The input apparatus 915 may be a remote control device that uses, for example, infrared radiation and another type of radiowave. Alternatively, the input apparatus 915 may be an external connection apparatus 929 such as a mobile phone that corresponds to an operation of the information processing apparatus 900. The input apparatus 915 includes an input control circuit that generates input signals on the basis of information which is input by a user to output the generated input signals to the CPU 901. A user inputs various types of data to the information processing apparatus 900 and instructs the information processing apparatus 900 to perform a processing operation by operating the input apparatus 915.

The output apparatus 917 includes an apparatus that can report acquired information to a user visually, audibly, or haptically. The output apparatus 917 may be, for example, a display device such as a liquid crystal display (LCD) or an organic electro-luminescence (EL) display, an audio output apparatus such as a speaker or a headphone, or a vibrator. The output apparatus 917 outputs a result obtained through a process performed by the information processing apparatus 900, in the form of video such as text and an image, sounds such as voice and audio sounds, or vibration.

The storage apparatus 919 is an apparatus for data storage that is an example of a storage unit of the information processing apparatus 900. The storage apparatus 919 includes, for example, a magnetic storage device such as a hard disk drive (HDD), a semiconductor storage device, an optical storage device, or a magneto-optical storage device. The storage apparatus 919 stores therein the programs and various data executed by the CPU 901, various data acquired from an outside, and the like.

The drive 921 is a reader/writer for the removable recording medium 927 such as a magnetic disk, an optical disc, a magneto-optical disk, and a semiconductor memory, and built in or externally attached to the information processing apparatus 900. The drive 921 reads out information recorded on the mounted removable recording medium 927, and outputs the information to the RAM 905. The drive 921 writes the record into the mounted removable recording medium 927.

The connection port 923 is a port used to connect devices to the information processing apparatus 900. The connection port 923 may include a Universal Serial Bus (USB) port, an IEEE1394 port, and a Small Computer System Interface (SCSI) port. The connection port 923 may further include an RS-232C port, an optical audio terminal, a High-Definition Multimedia Interface (HDMI) (registered trademark) port, and so on. The connection of the external connection device 929 to the connection port 923 makes it possible to exchange various data between the information processing apparatus 900 and the external connection device 929.

The communication apparatus 925 is a communication interface including, for example, a communication device for connection to a communication network 931. The communication apparatus 925 may be, for example, a communication card for a local area network (LAN), Bluetooth (registered trademark), Wi-Fi, or a wireless USB (WUSB). The communication apparatus 925 may also be, for example, a router for optical communication, a router for asymmetric digital subscriber line (ADSL), or a modem for various types of communication. For example, the communication apparatus 925 transmits and receives signals in the Internet or transits signals to and receives signals from another communication device by using a predetermined protocol such as TCP/IP. The communication network 931 to which the communication apparatus 925 connects is a network established through wired or wireless connection. The communication network 931 may include, for example, the Internet, a home LAN, infrared communication, radio communication, or satellite communication.

The example of the hardware configuration of the information processing apparatus 900 has been described. Each of the structural elements described above may be configured by using a general purpose component or may be configured by hardware specialized for the function of each of the structural elements. The configuration may be changed as necessary in accordance with the state of the art at the time of working of the present disclosure.

(7. Supplement)

The embodiment of the present disclosure can include the optical unit, the measurement system, and the measurement method described in the above, or an information processing apparatus (analysis unit), an information processing method executed by the information processing apparatus, a program for causing the information processing apparatus to function, and a non-transitory tangible medium in which the program is recorded, for example.

The preferred embodiment(s) of the present disclosure has/have been described above with reference to the accompanying drawings, whilst the present disclosure is not limited to the above examples. A person skilled in the art may find various alterations and modifications within the scope of the appended claims, and it should be understood that they will naturally come under the technical scope of the present disclosure.

Further, the effects described in this specification are merely illustrative or exemplified effects, and are not limitative. That is, with or in the place of the above effects, the technology according to the present disclosure may achieve other effects that are clear to those skilled in the art from the description of this specification.

Additionally, the present technology may also be configured as below.

(1)
An optical unit that radiates a coherent light such that the coherent light is incident in a target region of speckle image capturing in accordance with a pattern that includes a bright region and a dark region located uniformly in at least one direction in the target region.

(2)
The optical unit according to (1), including:
a filter that blocks the coherent light radiated from a light source in accordance with the pattern.

(3)
The optical unit according to (2), in which
the filter includes an optical element that is capable of partially changing a transmittance for the coherent light.

(4)
The optical unit according to (1), including:
a light source that radiates the coherent light in accordance with the pattern.

(5)
The optical unit according to any one of (1) to (4), in which
the pattern includes a plurality of slit bright regions that extend in a common direction.

(6)
The optical unit according to any one of (1) to (5), in which
the pattern includes a slit bright region that extends in at least two directions.

(7)
The optical unit according to any one of (1) to (6), in which
the pattern includes spot bright regions scattered in the target region.

(8)
The optical unit according to (7), in which
the bright regions are a circle, an ellipse, or a polygon.

(9)
The optical unit according to (7) or (8), in which
the bright regions are scattered at regular intervals in the target region.

(10)
The optical unit according to any one of (1) to (9), in which
the target region includes a region on an epidermis of a living body.

(11)
The optical unit according to (10), in which
the target region includes the region on the epidermis corresponding to a blood vessel in the living body.

(12)
The optical unit according to (10), in which
the target region includes the region on the epidermis vibrated by voice of the living body.

(13)
The optical unit according to (1), in which
the coherent light is radiated to be incident in the target region in accordance with the pattern by transformation or interference after radiation.

(14)
A measurement system including:
an optical unit that radiates a coherent light such that the coherent light is incident in a target region in accordance with a pattern that includes a bright region and a dark region located uniformly in at least one direction in the target region;
a light reception unit that receives a reflected light of the coherent light in the target region; and
an imaging unit that captures an image of a speckle included in the reflected light.

(15)

A measurement method including:
radiating a coherent light such that the coherent light is incident in a target region in accordance with a pattern that includes a bright region and a dark region located uniformly in at least one direction in the target region;
receiving a reflected light of the coherent light in the target region; and
capturing an image of a speckle included in the reflected light.

REFERENCE SIGNS LIST 100 measurement system
110 light source
120 filter
130 light reception unit
140 imaging unit
150 analysis unit
160 output unit

The invention claimed is:

1. An apparatus, comprising:
a coherent light source configured to radiate coherent light; and
a filter that includes a liquid crystal element, wherein
the filter is configured to generate a pattern based on change in transmittance of the liquid crystal element for the coherent light,
the coherent light is incident on a target region based on the pattern,
the pattern includes a first plurality of bright regions that extends in a lateral direction in the pattern, and a second plurality of bright regions that extends in a vertical direction in the pattern,
each bright region of the first plurality of bright regions and the second plurality of bright regions has a respective width,
the respective width of each of the first plurality of bright regions is different,
the respective width of each of the second plurality of bright regions is different,
bright regions of the first plurality of bright regions in the pattern are in a descending order, of the respective width of the first plurality of bright regions, from an upper side of the pattern to a lower side of the pattern,
a size of the target region is expanded based on the pattern,
the coherent light is reflected from the target region, and
an imager captures a speckle image from the reflected coherent light.

2. The apparatus according to claim 1, wherein the filter is configured to block the coherent light radiated from the coherent light source based on the pattern.

3. The apparatus according to claim 1, wherein the coherent light is radiated based on the pattern.

4. The apparatus according to claim 1, wherein each of the first plurality of bright regions and the second plurality of bright regions corresponds to a plurality of slit bright regions.

5. The apparatus according to claim 1, wherein the target region includes a region on an epidermis of a living body.

6. The apparatus according to claim 5, wherein the target region includes the region on the epidermis corresponding to a blood vessel in the living body.

7. The apparatus according to claim 5, wherein the target region includes the region on the epidermis that is vibrated by voice of the living body.

8. The apparatus according to claim 1, wherein the coherent light is incident in the target region based on the pattern by one of transformation or interference after radiation.

9. The apparatus according to claim 1, wherein
the target region includes a region on an epidermis of a living body, and
change in the pattern, generated by the filter, is based on individual variation of the living body of a subject.

10. A measurement system, comprising:
a coherent light source configured to radiate coherent light;
a filter that includes a liquid crystal element, wherein
the filter is configured to generate a pattern based on change in transmittance of the liquid crystal element for the coherent light,
the coherent light is incident on a target region based on the pattern,
the coherent light is reflected from the target region,
the pattern includes a first plurality of bright regions that extends in a lateral direction in the pattern, and a second plurality of bright regions that extends in a vertical direction in the pattern,
each bright region of the first plurality of bright regions and the second plurality of bright regions has a respective width,
the respective width of each of the first plurality of bright regions is different,
the respective width of each of the second plurality of bright regions is different, and
bright regions of the first plurality of bright regions in the pattern are in a descending order, of the respective width of the first plurality of bright regions, from an upper side of the pattern to a lower side of the pattern;
a light receiver configured to receive the reflected coherent light, wherein a size of the target region is expanded based on the pattern; and
an imager configured to capture a speckle image from the reflected coherent light.

11. A measurement method, comprising:
in a measurement system:
radiating coherent light from a coherent light source;
filtering the radiated coherent light by a filter, wherein
the filter includes a liquid crystal element,
the filter generates a pattern based on change in transmittance of the liquid crystal element for the coherent light,
the coherent light is incident on a target region based on the pattern,
the coherent light is reflected from the target region,
the pattern includes a first plurality of bright regions that extends in a lateral direction in the pattern, and a second plurality of bright regions that extends in a vertical direction in the pattern,
each bright region of the first plurality of bright regions and the second plurality of bright regions has a respective width,
the respective width of each of the first plurality of bright regions is different;
the respective width of each of the second plurality of bright regions is different, and
bright regions of the first plurality of bright regions in the pattern are in a descending order, of the respective width of the first of plurality bright regions, from an upper side of the pattern to a lower side of the pattern;

receiving, by a light receiver, the reflected coherent light, wherein a size of the target region is expanded based on the pattern; and capturing, by an imager, a speckle image from the reflected coherent light.

* * * * *